United States Patent [19]

de la Torre

[11] Patent Number: 5,368,602
[45] Date of Patent: Nov. 29, 1994

[54] SURGICAL MESH WITH SEMI-RIGID BORDER MEMBERS

[76] Inventor: Roger A. de la Torre, 48 Dauphine Dr., St. Louis, Mo. 63367

[21] Appl. No.: 16,795

[22] Filed: Feb. 11, 1993

[51] Int. Cl.⁵ .............................................. A61B 17/00
[52] U.S. Cl. ...................................... 606/151; 602/44
[58] Field of Search ..................... 606/151; 602/44, 75, 602/76; 623/13, 18, 19

[56] References Cited

U.S. PATENT DOCUMENTS

| | | |
|---|---|---|
| 2,671,444 | 3/1954 | Pease, Jr. . |
| 3,054,406 | 9/1962 | Usher . |
| 3,124,136 | 3/1964 | Usher . |
| 3,372,696 | 3/1968 | Rudie . |
| 3,416,524 | 12/1968 | Meier . |
| 4,347,847 | 9/1982 | Usher . |
| 4,452,245 | 6/1984 | Usher . |
| 4,633,873 | 1/1987 | Dumican et al. . |
| 4,693,720 | 9/1987 | Scharnberg et al. ................. 623/66 |
| 4,769,038 | 9/1988 | Bendavid et al. . |
| 4,877,030 | 10/1989 | Beck et al. . |
| 5,116,357 | 5/1992 | Eberbach . |
| 5,122,155 | 6/1992 | Eberbach . |
| 5,141,515 | 8/1992 | Eberbach . |
| 5,147,374 | 9/1992 | Fernandez . |
| 5,176,692 | 1/1993 | Wilk et al. . |
| 5,195,542 | 3/1993 | Gazielly et al. ........................ 602/44 |
| 5,201,745 | 4/1993 | Tayot et al. . |
| 5,254,133 | 10/1993 | Seid . |
| 5,258,000 | 11/1993 | Gianturco . |
| 5,318,559 | 6/1994 | Mulhauser et al. . |

Primary Examiner—Stephen C. Pellegrino
Assistant Examiner—Gary Jackson
Attorney, Agent, or Firm—Rogers, Howell & Haferkamp

[57] ABSTRACT

The present invention pertains to a patch of flexible surgical mesh material having at least one elongated semi-rigid member secured to the mesh material for use in facilitating positioning of the mesh material in surgical operations. In variant embodiments of the invention a plurality of semi-rigid members are formed either integrally with the flexible mesh as a single unit of the same material, or as separate component parts secured to the mesh material.

25 Claims, 3 Drawing Sheets

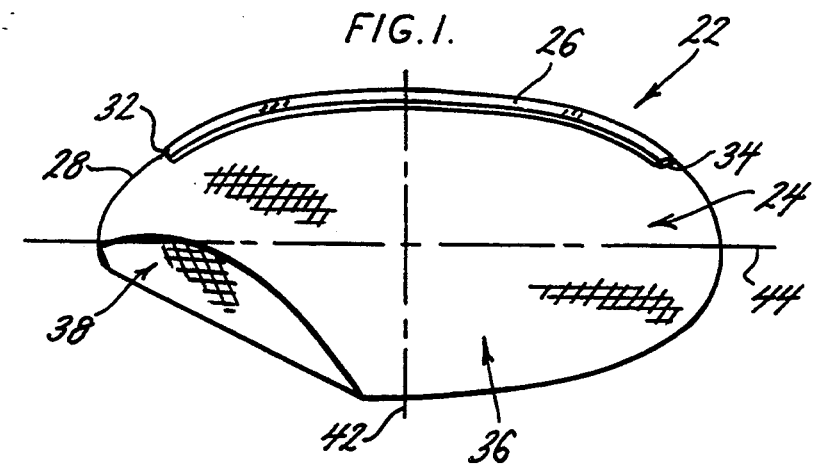
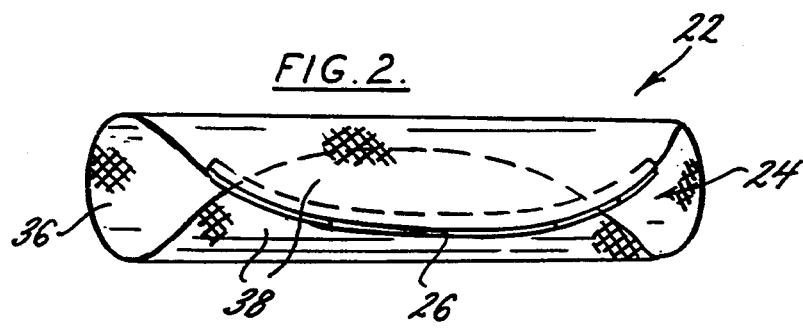
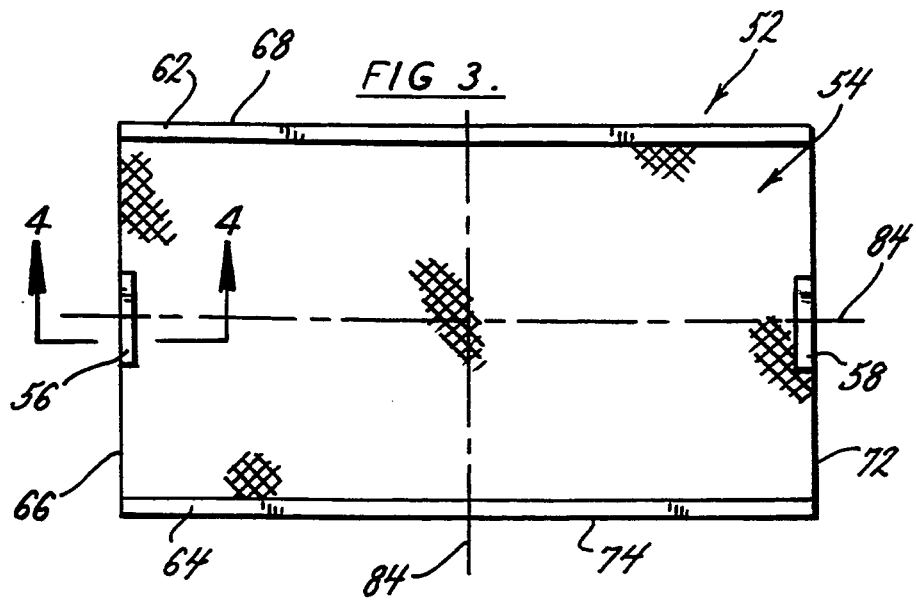
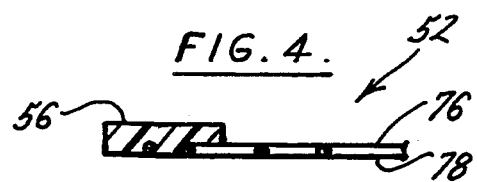

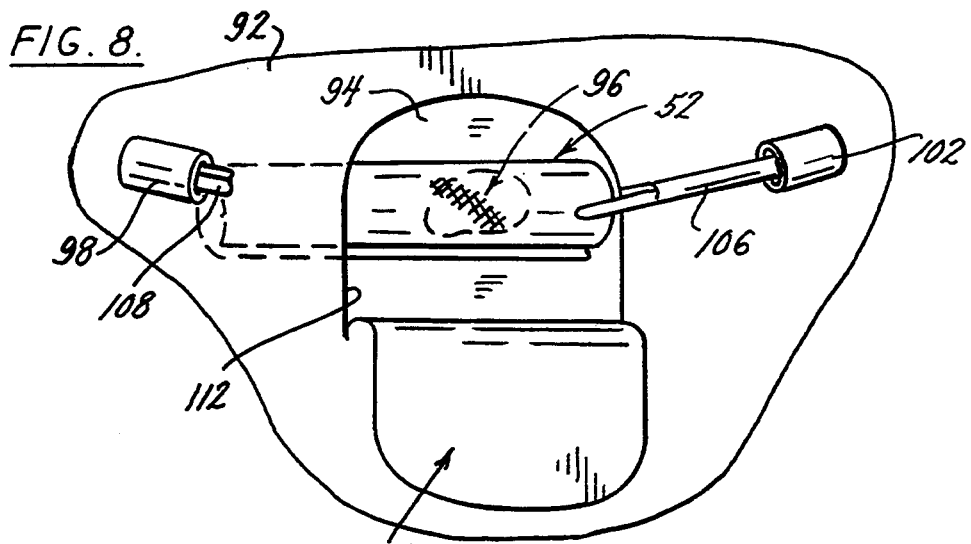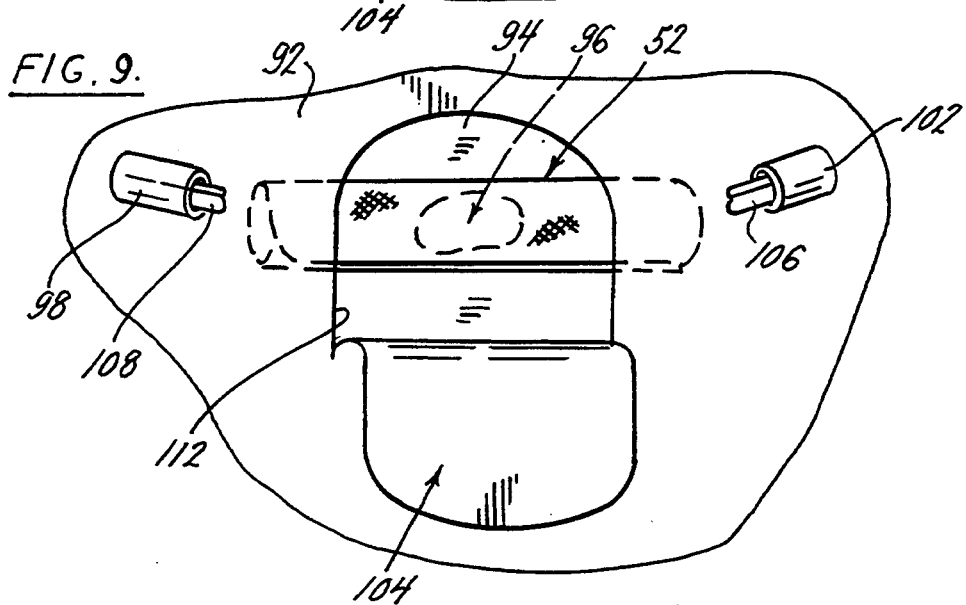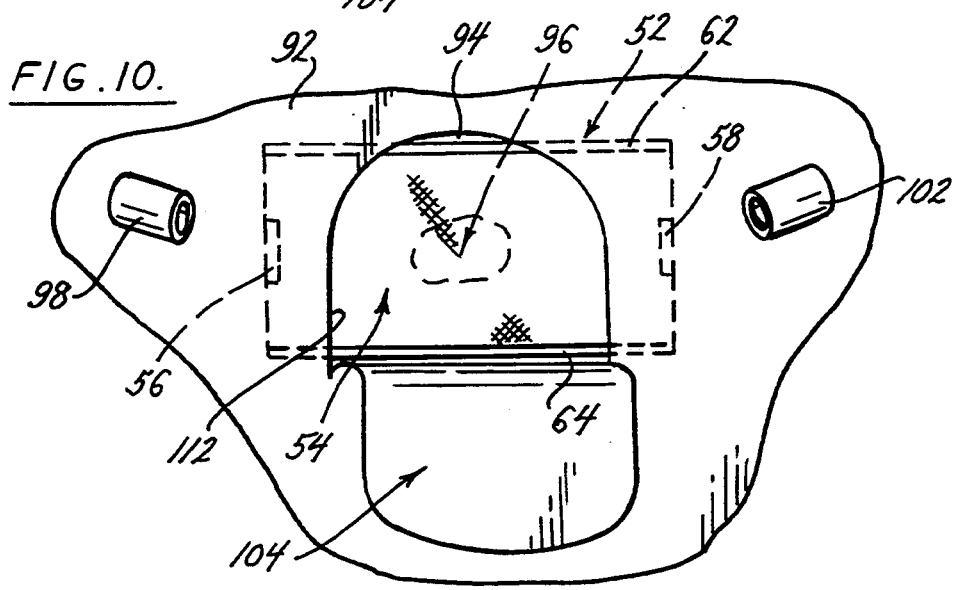

SURGICAL MESH WITH SEMI-RIGID BORDER MEMBERS

BACKGROUND OF THE INVENTION

1. Field of the Invention

The present invention pertains to a patch of flexible surgical mesh material having at least one elongated semi-rigid member comprised of or secured to the mesh material for use in facilitating positioning of the mesh material in surgical operations. In variant embodiments of the invention a plurality of semi-rigid members are formed either integrally with the flexible mesh as a single unit of the same material, or as separate component parts secured to the mesh material.

2. Description of the Related Art

Surgical mesh of various different types has long been known and used in the prior art. The known types of mesh material range from mesh constructed from resins such as that disclosed in the U.S. Pat. Nos. 2,671,444 of Pease, Jr. and Usher U.S. Pat. No. 3,124,136, to surgical mesh constructed of yarns or threads such as that disclosed in the U.S. Pat. No. 3,054,406, of Usher to surgical mesh constructed of absorbable or partially absorbable fibers such as that disclosed in the U.S. Pat. No. 4,633,873, of Dumican et al. Much of the prior art surgical mesh was designed for use in conventional surgery from exterior of the body where a large enough incision is made to provide ample access for the insertion of a patch of surgical mesh in a desired position or orientation in the body where reconstruction or repair is required. However, when employed with laparoscopic surgical techniques, difficulties are often encountered using conventional laparoscopic instruments in the insertion of conventional surgical mesh inside the body cavity through tubular trocars and in the subsequent positioning of the mesh in a desired orientation where reconstruction or repair is needed. Specialized surgical apparatus have been developed to facilitate the use of conventional surgical mesh in laparoscopic surgery, for example the apparatus disclosed in the U.S. Pat. No. 5,141,515 of Eberbach. However, it is still an often difficult and time consuming task to insert a patch of surgical mesh into a body cavity through a laparoscopic trocar, and then position the inserted mesh using laparoscopic instruments to an internal defect placing it against the defect where it is to be sutured.

It is an object of the present invention to provide an improved surgical mesh having a unique construction that facilitates the use of the mesh with laparoscopic surgical techniques as well as other surgical techniques.

It is a further object of the present invention to provide a surgical mesh having a unique construction that enables the mesh to be easily and quickly moved to and positioned in a desired location using conventional laparoscopic surgical instruments as well as other surgical instruments.

It is a still further object of the present invention to provide a surgical mesh of unique construction which assists in the mesh being unfolded and positioned contiguous with or overlapping an area of damaged tissue being reconstructed or repaired.

SUMMARY OF THE INVENTION

The surgical mesh of the present invention is generally comprised of a patch of flexible mesh material and one or more semi-rigid members each having an elongated configuration secured to the patch of mesh material. In the preferred embodiment of the invention, the one or more semi-rigid members are secured to the mesh material juxtaposed along portions of the border or peripheral edge of the patch. The rigid members may be secured permanently to the patch by being formed with the patch as a single unit of the same material or may be secured as a separate component part to the patch and be constructed of a different material from the patch, for example materials absorbable, partially absorbable or nonabsorbable by the human body. The configuration of the surgical mesh of the invention defined by the peripheral edge of the patch may be varied to best suit the particular application for which the surgical mesh is intended. The semi-rigid members are less flexible than the mesh material of the patch and the semi-rigidity of the members is sufficient to enable the manipulation and controlled positioning of the entire mesh area of the patch by simply grasping one end of the semi-rigid member and manipulating the member manually with conventional laparoscopic instruments. Moreover, the positioning of the one or more semi-rigid members on the mesh material of the patch enables the members to be used in positioning and unfolding the patch using conventional laparoscopic instruments and in overlaying an area of damaged tissue being reconstructed or mended by the surgical mesh.

BRIEF DESCRIPTION OF THE DRAWINGS

Further objects and features of the present invention are revealed in the following detailed description of the preferred embodiments of the invention and in the drawing figures wherein:

FIG. 1 shows a first embodiment of the surgical mesh of the invention;

FIG. 2 shows the mesh embodiment of FIG. 1 folded and rolled up for insertion through a laparoscopic trocar tube;

FIG. 3 shows a second embodiment of the surgical mesh of the invention;

FIG. 4 is a cross section view along the line 4—4 of FIG. 3;

FIG. 8 is a subsequent step to that shown in FIG. 7;

FIG. 9 is a subsequent step to that shown in FIG. 8; and

FIG. 10 is a subsequent step to that shown in FIG. 9.

DESCRIPTION OF THE PREFERRED EMBODIMENTS

Figure 5:
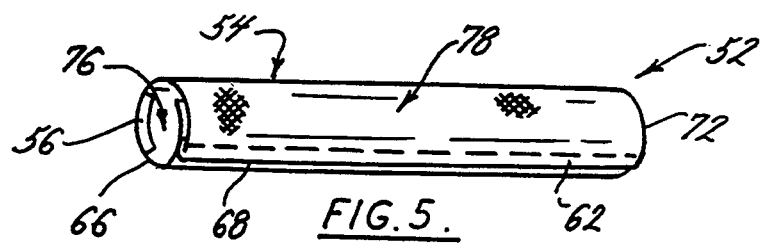
FIG. 5 shows the mesh embodiment of FIG. 3 folded and rolled up about an axis of the mesh.

The surgical mesh of the present invention is generally comprised of a patch of thin, flexible mesh material having any one of a variety of different configurations, the particular configuration of the mesh being chosen to best suit the intended application of the mesh in surgery. The surgical mesh of the invention also includes one or more semi-rigid, elongated border section members secured to the patch of mesh material. In variations of the invention both the patch of mesh material and the semi-rigid member or members may be constructed or formed integrally together as a single unit of the same material. The surgical mesh and the semi-rigid member or members may alternatively be constructed of different materials. For example, both the mesh and semi-rigid member or members may be constructed of known inert materials such as polypropylene or MARLEX ® mesh. MARLEX is a registered trademark of the Phillips Petroleum Company of Bartlesville, Okla. In a variant embodiment, both the mesh and the semi-rigid member or members may be constructed from tissue absorbable materials such as polyglycolic acid or from materials that are partially tissue absorbable such as combinations of polyglycolic acid fibers and non-absorbable fibers such as polypropylene. Still further, the patch of flexible mesh material may be constructed of an inert material where the semi-rigid member or members are constructed of tissue absorbable material, or the patch of mesh may be constructed of a tissue absorbable material where the rigid member or members are constructed of inert material. It should be understood that any of a wide variety of known inert and tissue absorbable materials may be employed in constructing the surgical mesh of the present invention and the materials set forth in the examples above are merely illustrative of the many possibilities.

A first embodiment of the surgical mesh 22 of the present invention is shown in FIGS. 1 and 2. This first embodiment of the surgical mesh is basically comprised of a patch of flexible mesh material 24 and an elongated semi-rigid member 26 secured to the patch. As shown in the drawing figures, the surgical mesh has a rounded or general oval configuration defined by the peripheral border or edge 28 of the patch. The oval configuration of the patch is illustrative only and it should be understood that the surgical mesh of the invention may have any one of a variety of different configurations with the particular configuration of the mesh being determined by the particular surgical application intended for the mesh. The thickness of the patch 24 is continuous within the peripheral edge 28 of the patch and is substantially the same as that of conventional surgical mesh. It can also be seen that the mesh material forming the patch 24 is continuous within the peripheral border or edge 28 of the patch with no holes or inconsistencies in the weave of the mesh. However, if for a particular application of the surgical mesh it is desired that there be a hole or a slit through the mesh material of the patch 24, such a hole or a slit can be easily provided by cutting through the material of the mesh.

In the first embodiment, the surgical mesh 22 comprises only a single, elongated semi-rigid member 26. The member 26 is shown secured along a portion of the peripheral border or edge 28 of the patch of mesh material. In variations of this embodiment, the semi-rigid member 26 may be positioned elsewhere on the area of the patch 24. The member 26 is formed integrally as a single unit with the patch 24 and is permanently secured to the patch. However, in variant embodiments the member may be removably secured to the patch 24 and may be constructed of a different material from that of the patch as explained above. The semi-rigid member 26 has opposite first 32 and second 34 ends spaced remote from each other by the length of the member. As shown in the drawing figures, the semi-rigid member 26 projects from the front surface 36 of the patch and does not extend from the rear surface 38. Alternatively, the semi-rigid member 26 may be secured to the patch so that a portion of the member's thickness projects from the front surface 36 of the patch and a portion of the member's thickness extends from the rear surface 38 of the patch.

The increased thickness of the semi-rigid member 26 and its more dense or semi-rigid construction gives the member a more rigid or less flexible character than that of the mesh material of the patch 24. Although less flexible than the mesh material of the patch, the semi-rigid member is still somewhat flexible. Because the semi-rigid member 26 is less flexible than the mesh material of the patch 24, the member 26 provides greater resistance to the patch being folded or rolled up about a lateral axis 42 of the patch that intersects the member 26 than being folded or rolled up about a longitudinal axis 44 of the patch that does not intersect the member 26. Moreover, by positioning the semi-rigid member 26 so that it extends longitudinally along a substantial portion of the longitudinal length of the patch mesh material as shown in the drawing figures, the patch may be folded and rolled up about its longitudinal axis 44 as shown in FIG. 2 to a compact configuration that is easily passed through a trocar for use of the mesh 22 in laparoscopic surgery. With the portion of the patch edge 28 having the member 26 secured thereto overlapping the rolled mesh material of the patch, the semi-rigid member 26 will serve in keeping any loose edges of the patch material from folding back or tending to unroll as the rolled surgical mesh 22 of the invention is pushed through the interior of a trocar tube and then later manipulated to where it is needed in laparoscopic surgery operations.

FIGS. 3–5 show a second, variant embodiment of the surgical mesh 52 of the present invention. The second embodiment of the surgical mesh 52 may be constructed of the identical materials as those described above with reference to the first embodiment and differs only from the first embodiment in its particular configuration and in that it consists of a plurality of semi-rigid members. Like the first embodiment, the second embodiment of the surgical mesh 52 is generally comprised of a patch 54 of flexible mesh material, a pair of semi-rigid members 56, 58 positioned at the longitudinally opposite edges of the patch, and a pair of semi-rigid members 62, 64 positioned at the laterally opposite edges of the patch.

As shown in the drawing figures, the surgical mesh 52 has a general rectangular configuration defined by four peripheral border or edge portions 66, 68, 72, 74 of the patch. As with the first embodiment, the rectangular configuration of the patch is illustrative only and the mesh of the invention may have any one of a variety of different configurations with the particular configuration of the mesh being determined by the particular surgical application intended for the mesh. However, the rectangular configuration shown in FIGS. 3–5 has the added advantage that it may be provided in a continuous roll of the mesh material of the invention. For example, the semi-rigid member 62 extending across the top of the patch 54 may have been cut from a continuous roll of mesh material where it was positioned adjacent another semi-rigid member corresponding to the bottom member 64 shown in FIG. 3 of the adjacent mesh patch on the roll. It can be appreciated that the manufacturer of the surgical mesh of the invention in a configuration such as that shown in FIGS. 3–5 where it can be produced on a continuous roll would be much less costly than producing individual surgical mesh patches such as that shown in FIGS. 1 and 2.

As in the first embodiment, the thickness of the patch 54 is continuous within the peripheral border 66, 68, 72, 74 and the mesh material itself is consistent within the border with no holes or inconsistencies in the mesh weave. However, the material of the surgical mesh 52 may be cut to best suit it for any desired application of the mesh. Although the semi-rigid members are less flexible than the material of the mesh, they too may cut using conventional surgical instruments to alter the configuration of the surgical mesh 52.

The four semi-rigid members 56, 58, 62, 64 are formed on the respective patch edge portions 66, 68, 72, 74 as separate component parts of the surgical mesh. Although permanently secured to the patch edge portions, the semi-rigid members are not formed of the same material as the patch 54 and are secured to the patch by being formed into the lattice of the patch mesh along their respective borders as illustrated in FIG. 4. However, in variant embodiments, the plurality of semi-rigid members 56, 58, 62, 64 may be constructed or formed integrally with the patch 54 as a single unit of the same material, as explained above. Still further, it may be desirable that the material of the laterally opposite semi-rigid members 62, 64 have different flexibility characteristics so that the mesh material of the patch 54 is more flexible than one of the semi-rigid members 64 while the one semi-rigid member 64 is more flexible than its laterally opposite semi-rigid member 62. The semi-rigid members 56, 58, 62, 64 of the embodiment of FIGS. 3–5 are shown projecting from the front surface 76 of the patch 24 of mesh material and being flush with the rear surface 78 of the patch. Alternatively, the semi-rigid members may be secured to the patch so that a portion of their thickness projects from both the front surface and the rear surface of the patch.

As in the first embodiment, although the plurality of semi-rigid members 56, 58, 62, 64 are less flexible than the mesh material of the patch 54, they are still somewhat flexible. Because the semi-rigid members are less flexible than the mesh material of the patch, the two laterally spaced members 62, 64 provide greater resistance to the patch being folded or rolled up about a lateral axis 82 of the patch that intersects the members than being folded or rolled up about a longitudinal axis 84 of the patch that does not intersect the members. With the longer pair of semi-rigid members 62, 64 positioned extending longitudinally across the entire length of the patch mesh material, the patch 54 may be folded and rolled up about its longitudinal axis 84 as shown in FIG. 5 to a compact configuration that is easily passed through a trocar tube for use of the mesh 52 in laparoscopic surgery. With the surgical mesh 52 rolled up as shown in FIG. 5, the laterally opposite rigid members 62, 64 extend along the length of the roll giving the entire roll of the mesh some rigidity and preventing the corners of the overlapping top edge 68 of the mesh from folding back or tending to unroll as the rolled surgical mesh 52 is pushed through the interior of a trocar tube and then later manipulated to where needed in laparoscopic surgery operations.

FIGS. 6–10 are schematic representations of the use of the second embodiment of the surgical mesh 52 in a laparoscopic surgical operation. The drawing figures and their description to follow only generally describe one use of the surgical mesh of the invention and are employed only to illustrate some benefits provided by the surgical mesh of the invention. Drawing FIGS. 6–10 and their description to follow describe use of the surgical mesh of the invention in laparoscopic surgery to mend a hernia. Again, it should be understood that the description to follow is illustrative only and should not be interpreted as limiting the use of the surgical mesh of the invention to only laparoscopic surgical techniques or only use in hernia operations. The benefits provided by the unique surgical mesh of the present invention suit it for use with a variety of different known surgical techniques and for use in at least those applications in which conventional surgical mesh is now employed.

Figure 6:
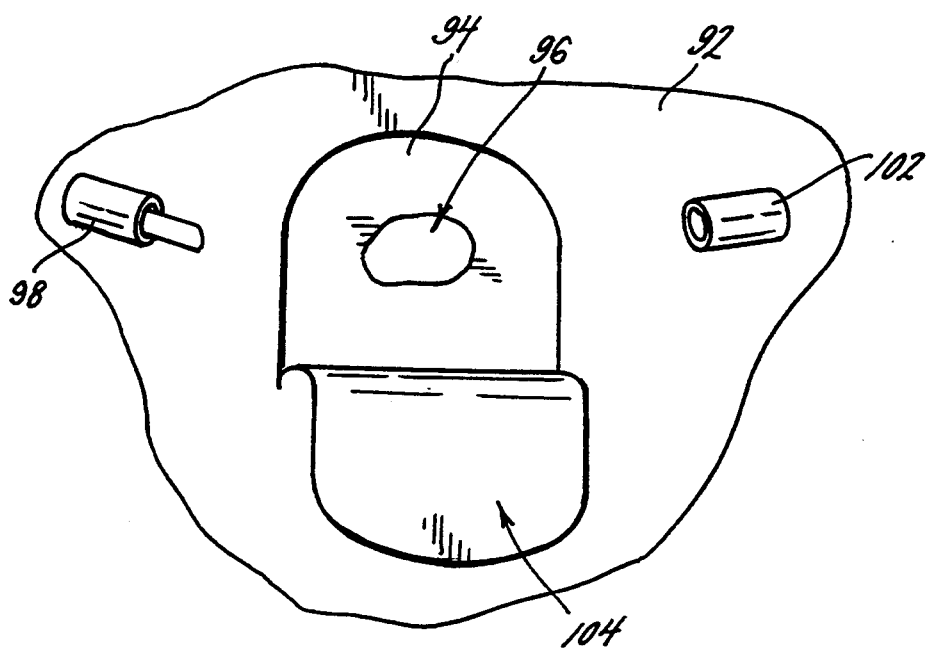
FIG. 6 is a schematic representation of a step involved in the use of the mesh of the invention in laparoscopic surgery.

FIG. 6 is a schematic representation of a view looking from inside the peritoneal cavity toward the peritoneum 92, the abdominal wall 94 and the defect to be repaired or mended by use of the surgical mesh of the invention, in this case a hernia opening 96. The drawing figure illustrates a laparoscopic repair of the hernia and a pair of trocars 98, 102 are shown already inserted through left and right flanks of the abdomen, respectively. Cautery scissors 104 are shown being retracted through the left trocar 98 after having made an incision through the peritoneum 92 to expose the hernia opening 96 in the abdomen wall 94. The portion of the peritoneum which formed the hernia sac 104 is shown lying within the peritoneal cavity below the hernia opening 96.

Figure 7:
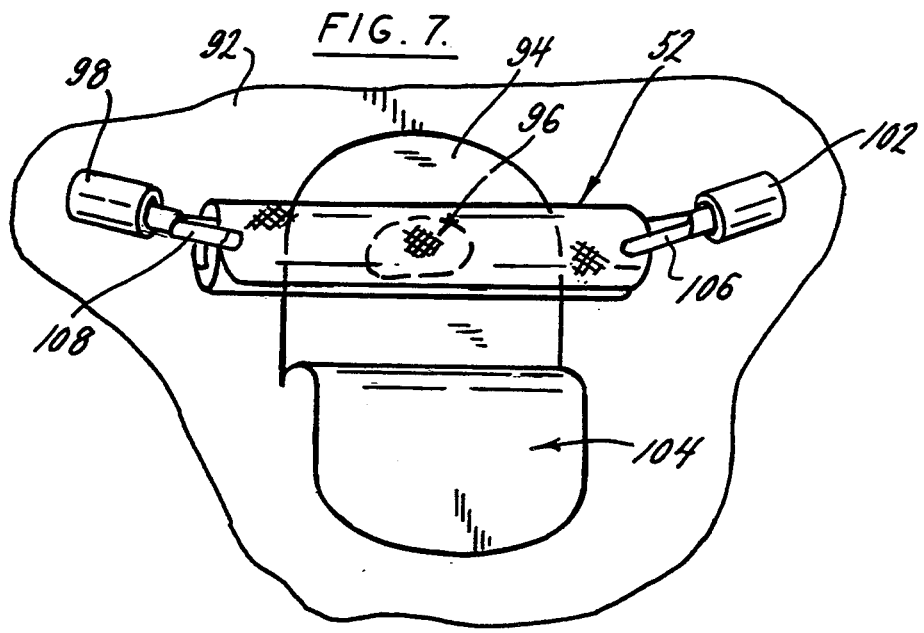
FIG. 7 is a subsequent step to that shown in FIG. 6.

In FIG. 7 the second embodiment of the surgical mesh 52 in its rolled up configuration has been inserted into the peritoneal cavity through the right trocar 102 by graspers 106 securely holding the right end of the rolled surgical mesh. Although not shown in FIG. 7, prior to the entire rolled surgical mesh being passed through the right trocar 102 and with the right hand portion of the rolled mesh still positioned within the trocar 102, a second grasper 108 is inserted through the left trocar 98 and securely grasps the left hand end of the rolled surgical mesh 52. With the two graspers 106, 108 securely holding the opposite ends of the rolled surgical mesh, the mesh is completely passed through the right trocar 102 and is positioned within the peritoneal cavity substantially as shown in FIG. 7.

In FIG. 8 the left hand end of the rolled surgical mesh 52 has been inserted beneath the incision 112 made through the peritoneum and placed between the peritoneum 92 and the abdominal wall 94. It should be appreciated that the semi-rigidity provided to the mesh 52 by the longitudinally extending semi-rigid members 62, 64 significantly facilitates the insertion of the mesh 52 beneath the peritoneum incision 112 and into the space between the peritoneum 92 and the abdomen wall 94. The flexibility of prior art surgical mesh would make such an insertion a very time consuming and difficult task. As shown in FIG. 8, due to the rigidity of the rolled mesh 52 provided by the longitudinal semi-rigid members 62, 64, the mesh 52 is easily inserted beneath the peritoneum incision 112 by manipulating the graspers 108, 106, then releasing the mesh from the left hand grasper 108, and then pushing the rolled mesh longitudinally further beneath the peritoneum 92 to the relative positions shown in FIG. 8.

In FIG. 9, the right hand side of the rolled surgical mesh 52 has been positioned beneath the right side of the peritoneum incision 112 between the peritoneum 92 and the abdomen wall 94. Again, the semi-rigidity provided to the rolled surgical mesh 52 by the longitudinal semi-rigid members 62, 64 greatly facilitates the insertion of the mesh beneath the peritoneum incision 112 and between the peritoneum and abdomen wall. The flexibility of prior art surgical mesh makes such a step very difficult and very time consuming.

With the rolled surgical mesh 52 now inserted between the peritoneum 92 and the abdomen wall 94 over the hernia opening 96, the mesh is next laid flat against the abdomen wall 94 over the hernia 96 as shown in FIG. 10. This step is accomplished by merely grasping a portion of the longitudinally extending semi-rigid member 62 with either of the graspers 106, 108 and moving the semi-rigid member 62 upward as viewed in the drawing figures. The semi-rigidity of the member 62 will cause the entire longitudinal length of the top of the patch 54 to spread together beneath the peritoneum 92 and over the abdomen wall 94. One of the two graspers 106, 108 next grip the lower longitudinally extending semi-rigid member 64 and manipulate this member downward causing the lower portion of the mesh patch 54 to be spread over the abdomen wall 94 beneath the peritoneum 92. Again, the semi-rigidity of the lower longitudinal member 64 assists in spreading the entire longitudinal length of the mesh patch 54 over the abdomen wall beneath the peritoneum with no folds being formed in the patch. The mesh 52 is then secured in place and the incision 112 through the peritoneum closed in the conventional manner.

It should be appreciated that the semi-rigid members 62, 64 extending longitudinally over the mesh patch 54 from one area of the patch adjacent its right side to another area of the patch adjacent its left side enable the entire longitudinal length of the mesh patch 54 to be manipulate simply by grasping either of the rigid members 62, 64 at any point along their lengths and manipulating manually the rigid members. The flexibility of conventional surgical mesh would have required significantly more time and more effort to completely spread the prior art mesh material over the hernia opening 96 and between the peritoneum 92 and the abdomen wall 94 to the position of the mesh of the invention 52 shown in FIG. 10. In the manner described above, the variant embodiments of the surgical mesh 22, 52 of the present invention significantly facilitate the manipulation and controlled positioning of the mesh patch 24, 54 than has been heretofore possible with prior art surgical mesh.

While the present invention has been described by reference to a specific embodiment, it should be understood that modifications and variations of the invention may be constructed without departing from the scope of the invention defined in the following claims.

What is claimed is:

1. In a surgical mesh for overlaying a body tissue opening to cover the opening and allow for tissue ingrowth within the surgical mesh, the improvement comprising:
a thin patch of flexible mesh material, the patch having an area configuration defined by a peripheral edge extending completely around a periphery of the patch, the peripheral edge having substantially the same flexibility as the mesh material of the patch;
at least one semi-rigid member having a length with opposite first and second ends, the member having a narrow, elongated configuration and a cross-sectional width that is larger than a thickness of the patch mesh material, the member being permanently secured along its length to the patch mesh material, and the member having less flexibility than the flexibility of the patch peripheral edge and the mesh material of the patch.

2. The surgical mesh of claim 1, wherein:
the patch mesh material and the semi-rigid member are formed together as a single unit of the same material.

3. The surgical mesh of claim 1, wherein:
the patch mesh material is formed of inert material and the semi-rigid member is formed of tissue absorbable material.

4. The surgical mesh of claim 1, wherein:
the semi-rigid member has a continuous length between its opposite first and second ends.

5. The surgical mesh of claim 1, wherein:
the patch of mesh material has first and second portions of its peripheral edge on longitudinally opposite sides of the area of the patch;
the semi-rigid member extends along the patch from the one end of the member adjacent the first portion of the peripheral edge to the second end of the member adjacent the second portion of the peripheral edge, and the semi-rigidity of the member is sufficient to enable the entire area of the patch to be manipulated and controllably positioned by the semi-rigid member in response to the semi-rigid member being grasped and manually manipulated.

6. The surgical mesh of claim 1, wherein:
the patch of flexible mesh has opposite front and back surfaces and the semi-rigid member is secured to only one of the surfaces with the cross-sectional width of the member projecting the member out from the one surface of the patch.

7. The surgical mesh of claim 1, wherein:
the first and second ends of the semi-rigid member are juxtaposed with longitudinally opposite first and second portions of the peripheral edge of the patch.

8. The surgical mesh of claim 7, wherein:
the length of the semi-rigid member is juxtaposed with the peripheral edge of the patch.

9. The surgical mesh of claim 1, wherein:
the configuration and rigidity of the semi-rigid member and the configuration and flexibility of the patch enable the patch to be folded and rolled up around the length of the rigid member in a compact tubular configuration of the surgical mesh.

10. The surgical mesh of claim 1, wherein:
a second semi-rigid member having a length with opposite first and second ends, a narrow elongated configuration and a cross-sectional width that is larger than the thickness of the patch mesh material, the second semi-rigid member is permanently secured to the patch mesh material in a position separated from the one semi-rigid member, and the second semi-rigid member has less flexibility than the flexibility of the mesh material of the pitch.

11. The surgical mesh of claim 10, wherein:
the one semi-rigid member has less flexibility than the second semi-rigid member, and the second semi-rigid member has less flexibility that the flexibility of the mesh material of the patch.

12. The surgical mesh of claim 10, wherein:
the patch mesh material and the one and second semi-rigid members are formed together as a single unit of the same material.

13. The surgical mesh of claim 10, wherein:
the one and second semi-rigid members are spaced laterally from each other on the patch and the lengths of both the one and second semi-rigid members extend longitudinally along the patch.

14. The surgical mesh of claim 10, wherein:
the length of the one semi-rigid member is juxtaposed with the peripheral edge of the patch and the length of the second semi-rigid member is juxtaposed with the peripheral edge of the patch generally opposite the one semi-rigid member.

15. The surgical mesh of claim 14, wherein:
a portion of the peripheral edge of the patch extends between the first ends of the one and second semi-rigid members and a portion of the peripheral edge of the patch extends between the second ends of the one and second semi-rigid members.

16. In a surgical mesh for overlaying a body tissue opening to cover the opening and allow for tissue ingrowth within the surgical mesh, the improvement comprising:
a thin patch of flexible mesh material, the patch having an area configuration defined by a peripheral edge extending completely around a periphery of the patch and the mesh material being continuous and having no interruptions within the peripheral edge, the peripheral edge having substantially the same flexibility as the mesh material of the patch;
a first semi-rigid member having less flexibility than the peripheral edge and the mesh material of the patch, the first member having a length with opposite first and second ends, the first member having a narrow elongated configuration and a cross-sectional width that is larger than a thickness of the patch mesh material, the first semi-rigid member being secured along its length to the patch juxtaposed along a portion of the peripheral edge; and
a second semi-rigid member having less flexibility than the peripheral edge and the mesh material of the patch, the second member having a length with opposite first and second ends, the second member having a narrow elongated configuration and a cross-sectional width that is larger than a thickness of the patch mesh material, the second semi-rigid member being secured along its length to the patch spaced from the first semi-rigid member and juxtaposed along a portion of the peripheral edge.

17. The surgical mesh of claim 16, wherein:
the first and second semi-rigid members have less flexibility than the mesh material of the patch.

18. The surgical mesh of claim 16, wherein:
the first and second semi-rigid members and the mesh material of the patch are formed together as a single unit of the same material.

19. The surgical mesh of claim 16, wherein:
the first and second semi-rigid members extend along the patch from one area of the mesh material adjacent the first ends of the members to a second area of the mesh material adjacent the second ends of the members, and the semi-rigidity of both the first and second semi-rigid members is sufficient to enable the second area of the mesh material to be manipulated and controllably positioned by the second end of either of the semi-rigid rigid members in response to the first end of either of the semi-rigid members being grasped and manually manipulated.

20. The surgical mesh of claim 16, wherein:
the patch of mesh material has mutually perpendicular longitudinal and lateral axes, and the first and second semi-rigid members are positioned on the patch extending longitudinally and spaced laterally from each other and provide greater resistance to folding and rolling up the mesh material of the patch about the lateral axis than to folding and rolling up the mesh material of the patch about the longitudinal axis.

21. In a surgical mesh for overlaying an opening in a body tissue to cover the opening and allow for tissue ingrowth within the mesh, the improvement comprising:
a thin patch of flexible mesh material having opposite front and back surfaces, the patch having an area configuration defined by a peripheral edge extending completely around the area of the patch, the peripheral edge having substantially the same flexibility as the mesh material of the patch; and
a semi-rigid member having a length with opposite first and second ends, the member being secured to only a portion of the peripheral edge of the patch, the member having less flexibility than the flexibility of the peripheral edge and mesh material of the patch and the member having a rigidity and a configuration on the patch that projects the member uprightly out from the front surface of the patch whereby the member provides means on the patch for grasping by a surgical grasper and manipulating the means by the grasper and thereby simultaneously manipulating the entire area of the patch while resisting folding of the patch at its peripheral edge as the patch is manipulated.

22. The improvement of claim 21, wherein:
the patch has mutually perpendicular longitudinal and lateral dimensions with the longitudinal dimension being at least as large as the lateral dimension; and
the semi-rigid member has a length with opposite first and second ends and a narrow, elongated configuration between its opposite first and second ends, and the semi-rigid member is secured to the patch with its length extending longitudinally along the patch peripheral edge.

23. The improvement of claim 21, wherein:
the semi-rigid member is secured to one surface of the front and back surfaces of the patch and the configuration of the member projects the member out from the one surface where the member can be grasped by a surgical grasper positioned directly over the one surface and the semi-rigid member.

24. The improvement of claim 23, wherein:
the semi-rigid member has a length with opposite first and second ends and a narrow, elongated configuration between is opposite first and second ends, and the semi-rigid member has a cross-sectional width that projects the member out from the one surface of the patch where the member can be grasped by a surgical grasper positioned directly over the one surface and the semi-rigid member.

25. The improvement of claim 21, wherein:
the semi-rigid member has a configuration on the patch that enables the area of the patch and the patch peripheral edge not secured to the semi-rigid member to be rolled up around the semi-rigid member into a compact tubular configuration of the patch that enables the surgical mesh to be inserted through a surgical trocar.

* * * * *